US009662621B2

(12) United States Patent
Beyer et al.

(10) Patent No.: US 9,662,621 B2
(45) Date of Patent: May 30, 2017

(54) DRUG RECONSTITUTION SYSTEM (71) Applicant: SENSILE PAT AG, Haegendorf (CH)

(72) Inventors: Uwe Beyer, Olten (CH); Derek Brandt, Oberdorf (CH); Thomas Gerber, Bern (CH); Franck Robin, Lenzburg (CH)

(73) Assignee: SENSILE PAT AG, Haegendorf (CH)

( * ) Notice: Subject to any disclaimer, the term of this patent is extended or adjusted under 35 U.S.C. 154(b) by 302 days.

(21) Appl. No.: 14/383,141

(22) PCT Filed: Mar. 4, 2013

(86) PCT No.: PCT/IB2013/051709
§ 371 (c)(1),
(2) Date: Sep. 5, 2014

(87) PCT Pub. No.: WO2013/132414
PCT Pub. Date: Sep. 12, 2013

(65) Prior Publication Data
US 2015/0029816 A1    Jan. 29, 2015

(30) Foreign Application Priority Data
Mar. 9, 2012 (CH) ......................................... 337/12

(51) Int. Cl.
B01F 15/02    (2006.01)
B01F 15/00    (2006.01)
(Continued)

(52) U.S. Cl.
CPC ........... B01F 15/00487 (2013.01); A61J 1/20 (2013.01); A61M 5/14216 (2013.01);
(Continued)

(58) Field of Classification Search
CPC ............ B01F 15/00487; B01F 15/0243; B01F 2215/0034; A61M 5/14216;
(Continued)

(56) References Cited

U.S. PATENT DOCUMENTS 4,184,815 A * 1/1980 Casson ................. A61M 5/142
417/477.7
4,278,085 A * 7/1981 Shim ................. A61M 5/14232
128/DIG. 12
(Continued)

FOREIGN PATENT DOCUMENTS

EP    2 172 182 A2    4/2010
EP    2 236 077    10/2010
(Continued)

OTHER PUBLICATIONS

Written Opinion in International Application No. PCT/IB2013/051709, Jul. 26, 2013, pp. 1-5.
(Continued)

Primary Examiner — Tony G Soohoo
(74) Attorney, Agent, or Firm — Saliwanchik, Lloyd & Eisenschenk (57) ABSTRACT A drug reconstitution device comprising a disposable liquid transfer unit (18) and a reusable control and drive unit (16) removably connectable to the liquid transfer unit, the liquid transfer unit including a housing (26), a docking interface (30) configured for coupling at least one of the first and second constituent containers (2, 4) to the housing (10), and a pump engine (28) and fluid flow system (36) configured for transferring liquid from the first constituent container (2) to the second constituent container (4). The control and drive unit comprises a pump drive (22) configured to drive the pump engine during a liquid transfer action, the pump drive comprising a transmission output coupling (34) removably engaged with a transmission input coupling (50) of the pump
(Continued)

engine (28) when the liquid transfer unit and control and drive unit are connected.

34 Claims, 4 Drawing Sheets

(51) Int. Cl.
*A61J 1/20* (2006.01)
*A61M 5/142* (2006.01)
*A61M 5/14* (2006.01)
*A61M 5/168* (2006.01)

(52) U.S. Cl.
CPC ..... *A61M 5/14248* (2013.01); *B01F 15/0243* (2013.01); *A61J 1/201* (2015.05); *A61J 1/2013* (2015.05); *A61M 5/142* (2013.01); *A61M 5/1413* (2013.01); *A61M 5/14236* (2013.01); *A61M 5/16827* (2013.01); *B01F 2215/0034* (2013.01)

(58) Field of Classification Search
CPC .............. A61M 5/14248; A61M 5/142; A61M 5/1413; A61M 5/14236; A61M 5/16827; A61J 1/20; A61J 1/201; A61J 1/2013
See application file for complete search history.

(56) References Cited

U.S. PATENT DOCUMENTS

| | | | | |
|---|---|---|---|---|
| 4,968,229 A | * | 11/1990 | Neuder | A61M 5/142 417/474 |
| 5,304,165 A | * | 4/1994 | Haber | A61J 1/2089 604/411 |
| 5,329,976 A | * | 7/1994 | Haber | A61J 1/2089 141/18 |
| 8,282,366 B2 | | 10/2012 | Hilber et al. | |
| 2006/0051217 A1 | * | 3/2006 | Felton | F04C 5/00 417/410.1 |
| 2009/0062732 A1 | * | 3/2009 | Radmer | A61M 39/22 604/84 |
| 2009/0099547 A1 | * | 4/2009 | Radmer | A61J 1/2089 604/519 |
| 2009/0123309 A1 | * | 5/2009 | Hilber | A61M 5/14244 417/417 |
| 2012/0022354 A1 | | 1/2012 | Beyer et al. | |
| 2013/0017099 A1 | * | 1/2013 | Genoud | A61M 5/14216 417/53 |
| 2015/0029816 A1 | * | 1/2015 | Beyer | A61J 1/20 366/167.1 |

FOREIGN PATENT DOCUMENTS

| | | |
|---|---|---|
| WO | WO 96/26702 | 9/1996 |
| WO | WO 02/094356 | 11/2002 |
| WO | WO 2007/074363 | 7/2007 |
| WO | WO 2007/107406 | 9/2007 |
| WO | WO 2007/147741 | 12/2007 |
| WO | WO 2011/071952 | 6/2011 |
| WO | WO 2011/114285 | 9/2011 |
| WO | WO 2012/019642 | 2/2012 |

OTHER PUBLICATIONS

George Roessling, PhD; "Micropumps for a Novel Combination Device: Lyo Reconstitution and Injection"; whole document; Nov. 9, 2011; PDA Europe Conference, Basel, Switzerland, total 17 pages.†

\* cited by examiner
† cited by third party

DRUG RECONSTITUTION SYSTEM

CROSS-REFERENCE TO RELATED APPLICATION

This application is the U.S. national stage application of International Patent Application No. PCT/IB2013/051709, filed Mar. 4, 2013.

The present invention relates to a drug reconstitution system, in particular for the reconstitution of a drug from two constituents where at least one constituent is a liquid. The other constituent may in particular be in a dry form, such as a lyophilized substance.

Certain pharmaceutical products are only available in lyophilized form due to enhanced stability of the products for easier transport and storage. These products need to be dissolved prior to the administration of the product to a patient. There might also be other reasons why the active substance or product is lyophilized and not in the form of a liquid or solution, such as deficient stability when in contact with oxygen or air.

Typically the lyophilized substance is portioned in containers such as ampoules or vials and sealed by a septum which is fixed by a crimped cap. In some cases a separate container with the exactly dosed diluent is delivered or available together with the container comprising the lyophilized substance. In other cases the amount of diluent has to be dosed during drug reconstitution. Before administration to a patient the lyophilized substance has to be dissolved or reconstituted with the diluent. The diluent may be a physiological saline solution or another aqueous formulation. The reconstitution of a lyophilized substance may typically require the following steps in sequence:

Unpacking a disposable sterile syringe,
Connecting the syringe with a sterile cannula,
Filling the syringe with air by moving a piston of the syringe,
Using a sharp tip of the syringe cannula to perforate a septum of a vial or container comprising the diluent,
Injecting the air contained in the syringe into the vial or container,
Filling the syringe with the exact amount of diluent needed to dissolve the lyophilized substance,
Removing the cannula from the vial or container,
Using the sharp tip to perforate a septum of a vial or container comprising the lyophilized substance,
Injecting the diluent into the vial comprising the lyophilized substance,
Manually supporting the dissolving of the lyophilized substance in the diluent by gently shaking the vial and the syringe,
Carefully filling the syringe with the dissolved substance,
Checking for air bubbles in the syringe, and
Administration of the dissolved substance to a patient, for example by injection directly with the syringe or via an infusion system over a certain period.

The manual dissolving of a lyophilized substance with a syringe comprising a cannula requires a number of steps as shown above, whereby each of these steps may contain a potential source of error or false manipulation. Besides that these steps are time-consuming and have to be carried out exactly, carefully and in certain applications quite quickly because the lyophilized substance may react with oxygen or other substances and lose its active properties. Additionally, the administration and manipulation with a syringe comprising a cannula with a sharp tip allowing the perforation of the septum may raise the risk of injuring a person.

Some techniques and devices to simplify the process of the reconstitution of a lyophilized substance are known from the prior art. Typically such a device comprises two vials or chambers in which one vial or chamber comprises the lyophilized substance and the other vial or chamber the diluent.

Such a device and method is shown for example in EP 1 287 841 A2. The device comprises one single syringe with a first end configured to be connected to a cannula and a second end which receives a plunger configured to be moved by a piston rod. A first chamber, which is arranged adjacent to the first end, comprises a poorly soluble pharmaceutical substance such as a lyophilized substance. A second chamber adjacent to the first chamber and separated by the first chamber by a central plunger comprises the diluent. The plunger mounted on the piston rod closes the second chamber. By pushing the piston rod towards the first end of the syringe, the central plunger is moved towards a bypass formed in the wall of the syringe, allowing part of the diluent to flow into the first chamber and mix with the poorly soluble substance. By pulling the piston rod back, away from the first end, the now liquid substance, comprising a part of the diluent and a part of the poorly soluble substance, is drawn back into the second chamber. Then the piston rod is moved again towards the first end in order to mix more diluent with the poorly soluble substance. These push and pull operations of the piston rod may be repeated until the poorly soluble substance is completely dissolved in the diluent. A syringe according to EP 1 287 841 A2 is however quite bulky, long and its manufacturing is complex. Besides that, the diluent in the second chamber has to be exactly pre-dosed and cannot be adjusted during the administration of the substance. Additionally it comprises a cannula having a free end with a sharp tip, raising the risk of injury.

Another device is known from U.S. Pat. No. 6,238,372 B1, which discloses an adapter configured to be connected to a vial comprising the lyophilized substance. The adapter comprises an opening which is configured to receive a syringe pre-filled and pre-dosed with the diluent. After connecting the syringe to the adapter, the piston of the syringe may be pushed so that the diluent flows into the vial, which then starts the dissolving process. The dissolving process is supported by gently shaking the vial with the adapter and the syringe. Once the lyophilized substance is completely dissolved, the vial is turned upside-down and the piston of the syringe is pulled back in order to fill the syringe. In a next step the filled syringe comprising the reconstituted substance and the adapter are disconnected from the vial. Said disconnecting operation opens a channel from the syringe chamber to an injecting needle and can be administered to a patient. In a variant a similar adapter may be used to connect two vials, a first vial comprising the lyophilized substance under vacuum and the second vial comprising the diluent, as shown in U.S. Pat. No. 6,558,365 B2. When the second vial is connected to the adapter the vacuum draws the diluent into the first chamber through channels in the adapter. After gentle shaking, the reconstituted substance may be withdrawn into a syringe, whereby the first vial must be pressurized by the syringe before withdrawal, for example with air. In both aforementioned devices the reconstitution requires certain steps and the dissolving process is not well controlled. Some lyophilized substances may require a more sophisticated or controlled dissolving process due to poorly soluble properties. Besides that, some reconstituted substances may lose their active properties because of contact with oxygen or air. In addition, the dosage of the diluent is given and cannot be changed during the administration.

Devices for the reconstitution of a dry drug, where there is a disposable reservoir and a reusable pump device, are described in WO2011/071952 and WO2007/107406. The pump and fluid circulation systems of these devices are bulky and complex and prone to errors in the setup before a mixing process. The device in WO2007/107406 is bulky and pumps liquid from a reservoir to a vial and then directly to the patient, without additional control of the mixture of the reconstituted drug. This may cause problems if the reconstituted drug is not properly mixed. The device in WO2011/071952 uses a peristaltic or other form of external pressure pump to transfer liquid from one container to the other, whereby there is also a potential problem if the reconstituted drug is not properly mixed.

Further, in the above systems the containers can be removed from the pump unit and possibly reused, which creates a safety and hygiene risk.

An object of this invention is to provide a drug reconstitution system which is reliable, safe and easy to use.

It is advantageous to provide a drug reconstitution system that is economical to manufacture and use.

It is advantageous to provide a drug reconstitution system that is light, versatile and compact.

For certain applications it is advantageous to provide a drug reconstitution system which is easily portable and autonomous.

Objects of the invention have been achieved by providing a drug reconstitution device according to claim 1.

Disclosed herein is a drug reconstitution device comprising a disposable single-use liquid transfer unit and a reusable control and drive unit removably connectable to the liquid transfer unit, the liquid transfer unit including a housing, a docking interface configured for coupling at least one of a first and a second constituent container to the housing, and a pump engine and fluid flow system configured for transferring liquid from the first constituent container to the second constituent container. The control and drive unit comprises a pump drive configured to drive the pump engine during a fluid pumping action, the pump drive comprising a transmission output coupling removably engaged with a transmission input coupling of the pump engine when the liquid transfer unit and control and drive unit are connected. The pump engine is advantageously configured as a rotary pump and comprises a rotor rotatably movable in a stator and a transmission input coupling removably engageable with a transmission output coupling of the pump drive.

The pump engine rotor may advantageously be directly attached to the transmission input coupling.

The pump engine may advantageously be formed of polymers and integrally mounted in the liquid transfer unit as a single-use disposable unit.

In an embodiment, the docking interface comprises a first container docking interface configured to interconnect the first constituent container with the fluid flow system in a fluidic manner and a second container docking interface configured to interconnect the second constituent container with the fluid flow system in a fluidic manner.

The first docking interface may advantageously have a different shape or profile and/or size than the second docking interface, configured to prevent connection of the first constituent container in the second container docking interface and connection of the second constituent container in the first container docking interface.

The fluid flow system comprises a first fluidic channel and a second fluidic channel and the pump engine comprises a pump chamber, said first fluidic channel interconnecting the first container docking interface with the pump chamber in a fluidic manner and said second fluidic channel interconnecting the second container docking interface with the pump chamber in a fluidic manner.

The docking interface may advantageously comprise a locking mechanism configured to lock at least one of the first and second constituent containers to the housing when said constituent container is connected to the docking interface. In a variant, at least one locking mechanism is irreversible and configured to irremovably couple at least one container to the liquid transfer unit.

In a first variant, the pump engine is configured as a bi-directional pump.

In another variant, the pump engine is configured as a uni-directional pump.

The drug reconstitution device may advantageously be configured as a portable device, the control and drive unit comprising an autonomous power source.

The device may advantageously comprise a releasable locking mechanism configured to lock the control and drive unit to the liquid transfer unit to the control and drive unit during the liquid transfer operation.

The transmission output coupling of the pump drive may advantageously be in the form of a spring biased shaft.

Further objects and advantageous features of the invention will be apparent from the claims, the detailed description, and the annexed drawings, in which:

Referring to the figures, which show exemplary embodiments of the invention, a drug reconstitution system 1 comprises a drug reconstitution device 6 and connectable first and second constituent containers 2, 4. The drug reconstitution device 6 comprises a control and drive unit 16 and a liquid transfer unit 18, as best seen in FIGS. 1, 2, 3 and 6. The first and second constituent containers 2, 4 are configured to be connected to the liquid transfer unit 18.

The liquid transfer unit 18 is configured as a single-use disposable unit. The control and drive unit 16 is configured as a reusable unit. In a variant at least one of the first or second constituent containers 2, 4 are connected to the disposable liquid transfer unit 18 in a non-releasable manner in order to avoid the re-use of the first or second constituent containers 2, 4. In another variant, both constituent containers 2, 4 may be connected to the disposable liquid transfer unit 18 in a non-releasable manner, for instance when an additional adapter for an empty syringe or ampoule exists, which is filled with the reconstructed drug at the end of the drug reconstitution process. After the withdrawal of the container/syringe/ampoule with the reconstituted drug, the liquid transfer unit 18 can be disposed of together with the first constituent container 2 and/or the second constituent container 4.

The liquid transfer unit 18 comprises a housing 26, a pump engine 28 and a container docking or coupling interface 30. The pump engine 28 comprises a rotor 38 and a stator 40. The rotor 38 further comprises a transmission input coupling 50. The pump engine 28 may be configured as a micropump disclosed in WO2007074363. Such a micropump can be configured as a two-way pump such that the pump engine 28 can pump liquid from the first constituent container 2 to the second constituent container 4 and inversely.

The pump engine 28 further comprises a pump chamber 41, which is arranged between the rotor 38 and stator 40. The rotor 38 is configured to be axially movable as a function of the rotational movement, for instance as described in EP 1 699 859 or EP 1 803 934.

In order to ensure accurate reconstitution of the drug to be administered, the pump engine 22 is advantageously operable at a positive pressure upstream of the pump engine of up to 2 bars, and a negative pressure upstream of the pump engine of up to −0.4 bars, with a deviation of the delivered volume below 5%. Such a positive pressure may occur when the gas volume in one of the constituent containers 2, 4 is filled with liquid from the other container. In order to prime the liquid transfer unit 18 with diluent initially instead of the first constituent container, a priming vial (not shown) is connected to the adapter which can be disconnected, replaced by the first constituent container, and disposed of after the priming of the liquid transfer unit 18. A priming of the liquid transfer unit 18 may be necessary when the lyophilized substance is very sensitive to the surrounding air.

In a frequent application of a drug reconstitution system, one of the containers (in the embodiments illustrated the first constituent container 2) contains a lyophilized substance and the other container (in the embodiments illustrated the second constituent container 4) contains a solvent or diluent to dissolve the lyophilized substance.

In an advantageous embodiment, one of the two constituent containers 4 or 2 is configured to be irreversibly locked to the liquid transfer unit 18 once it is connected to the latter. The other of the two constituent containers 2 or 4 containing the reconstituted drug is configured to be removable from the liquid transfer unit 18. In case the container with the reconstituted drug is a vial with a septum, the reconstituted drug can be withdrawn by a syringe with a cannula. When the container containing the reconstructed drug is a cartridge with a piston, for example this may be mounted in a drug delivery device, such as an injection pen device, a patch pump device or other type of drug delivery device for administration of the drug to a patient.

In the case where the lyophilized substance is poorly dissolvable, the micropump may be used to enhance the mixing and dissolving process by pumping liquid from the first constituent container 2 to the second constituent container 4, then reversing the pumping direction back to the first constituent container 2, and repeating the back and forth pumping cycle until the lyophilized substance is completely dissolved. When the dissolving process is finished, the reconstituted drug can either be pumped into the first or second constituent container 2, 4.

Figure 1:
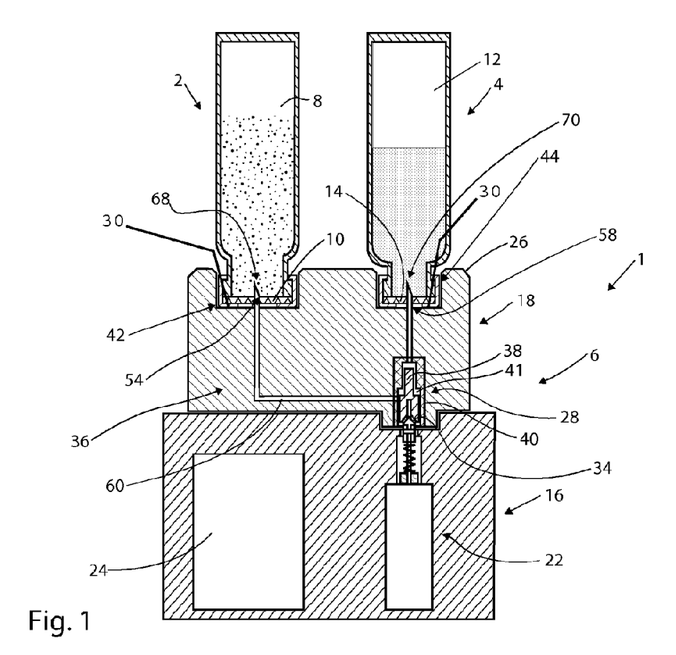
FIG. 1 is a cross-sectional view of a first embodiment of a drug reconstitution system according to the invention.
Figure 2:
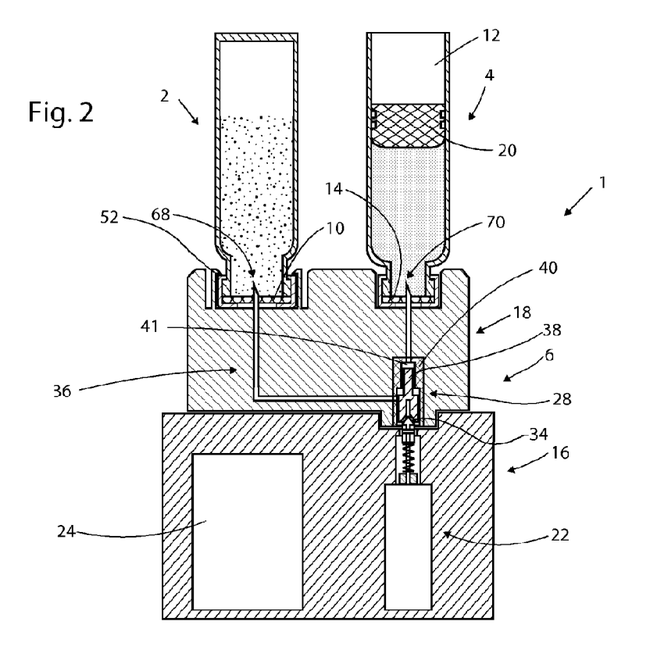
FIG. 2 is a cross-sectional view of another embodiment of a drug reconstitution system according to the invention.

In a variant, the reconstituted drug may be withdrawn from the container, for example by a syringe. In another variant, the container containing the reconstituted drug may be a syringe and the piston 20 of the cartridge 12 may be used to push the drug out of the syringe. A container 4 comprising the cartridge 12 and the piston 20 is shown in FIG. 2.

In another variant the liquid transfer unit comprises a valve mechanism 46 with a three-way valve 66. The three-way valve 66 may be used to divert the flow of the dissolved active substance from the second constituent container 4 to an injection system (not shown) or to an external connecting portion 48. Such an embodiment is shown for example in FIG. 6. The three-way valve 66 can also be arranged between the second constituent container 4 and the pump engine 28, configured to divert the flow of the reconstituted drug from the first constituent container 2 to the infusion set 32 or the external connecting portion 48.

The control and drive unit 16 comprises a power source and a pump drive 22 which is used to drive the pump engine 28 when the liquid transfer unit 18 is connected to the control and drive unit 16. The pump drive 22 comprises a transmission output coupling 34 configured to engage the transmission input coupling 50 on the rotor 38. The power source may advantageously be in the form of an autonomous power source such as an on-board battery or a rechargeable battery power source, such that the control and drive unit is configured as an autonomous portable unit. The control and drive unit 16 may further comprise electronics to control operation of the pump drive, including for instance the starting and stopping of the pump, the speed of the pump, measurement of the volume transferred, and alarms or other user signaling means to signal completion of the liquid transfer or other useful information.

Figure 3:
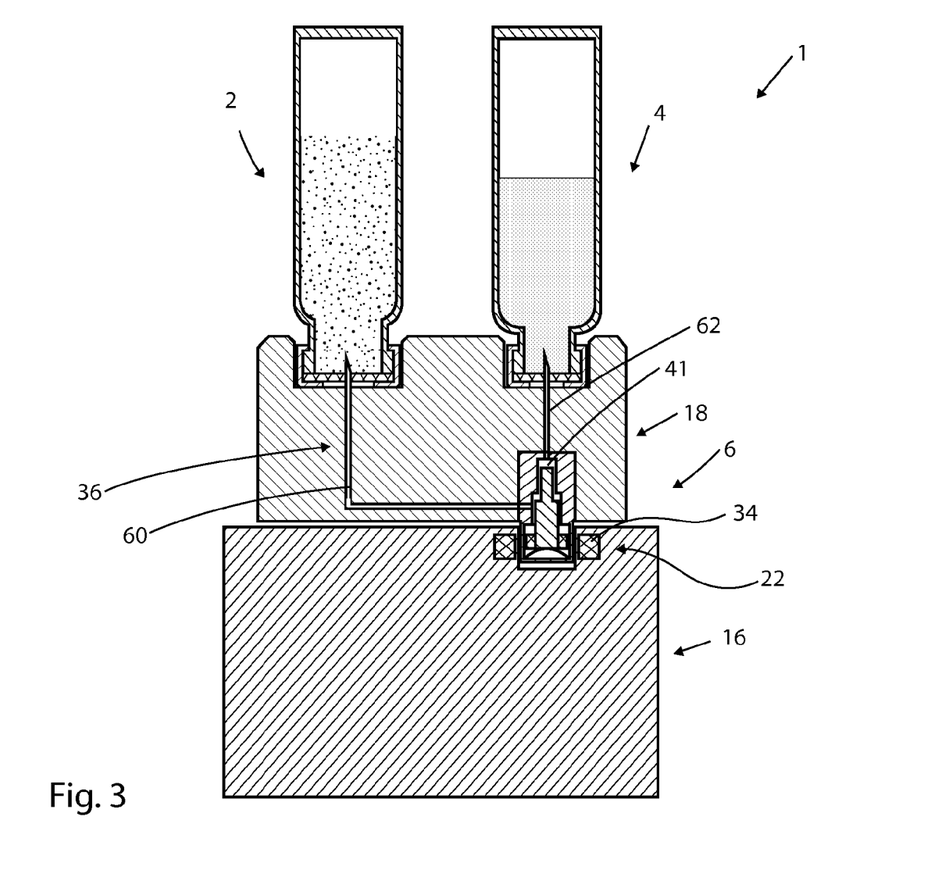
FIG. 3 is a cross-sectional view of another embodiment of a drug reconstitution system according to the invention.
Figure 4:
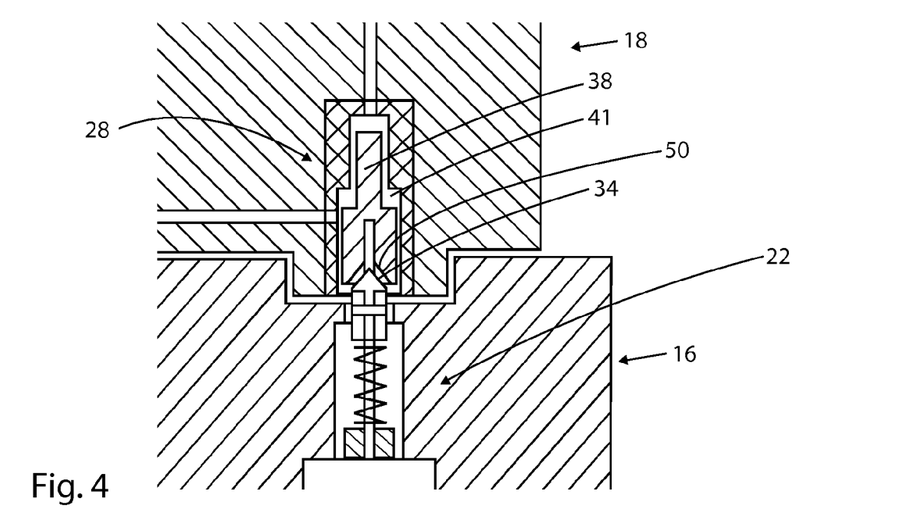
FIG. 4 is an enhanced cross-sectional view of a coupling between a pump engine and a pump drive of an embodiment similar to FIG. 1.
Figure 5:
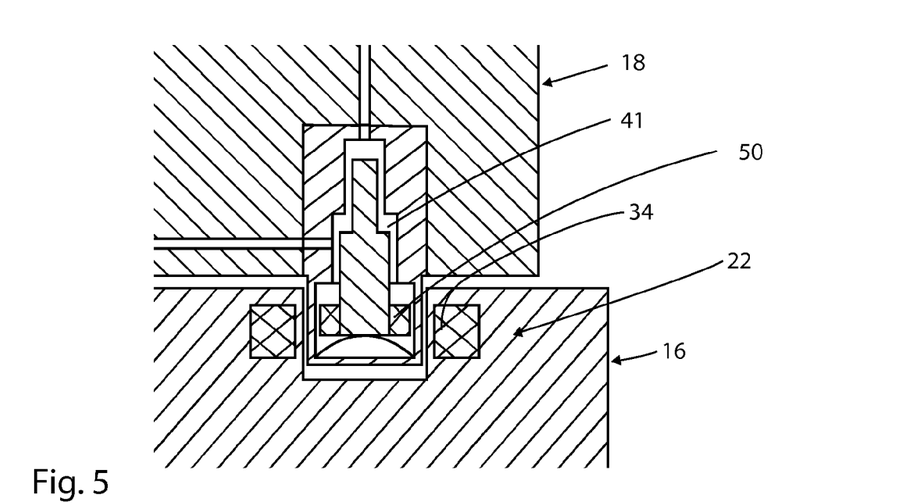
FIG. 5 is an enhanced cross-sectional view of a coupling between a pump engine and a pump drive of an embodiment similar to FIG. 3.

The pump drive 22 may comprise a shaft/spring mechanism as shown in FIGS. 1, 2, 4 and 6 or a magnetic drive comprising permanent magnets on the rotor 38, which engage with one or more permanent or electromagnets arranged around the rotor 38, as illustrated in the embodiment of FIGS. 3 and 5. The different embodiments shown in the figures may comprise a mechanical pump drive 22 having a shaft or a magnetic drive with electromagnets. The transmission output coupling 34 may be in the form of a mechanical coupling such as a splined, toothed, or non-cylindrical shaft which engages with a transmission input coupling 50 formed on the pump engine to transmit torque. The transmission input coupling 50 may be in the form of a recess with teeth as shown in FIG. 4, in which a shaft including complementary teeth of the transmission output coupling 34 may glide in during the connection of the control and drive unit 16 to the liquid transfer unit 18. When the control and drive unit is connected, the shaft may engage with the recess and the teeth therein, in order to transfer a torque or force from the pump drive to the pump engine. A mechanical coupling between the pump drive and the pump engine may also include a gear box or other torque multiplication or reduction mechanism arranged between the transmission output coupling 34 and the pump engine 28.

In an advantageous variant the pump engine 28 may have the function and features of a micropump such as disclosed in WO2007074363. The pump engine may advantageously be made of injected polymers to form the rotor, housing and seals in an economical manner adapted for single use and easy disposal.

The first and/or second constituent container 2 may be configured as a vial or pouch (not shown). It is further possible to have the constituent container comprising the solvent or diluent configured as a vial or pouch (not shown) comprising a quantity of liquid for more than one constituent container 2 comprising the lyophilized powder. The pouch may be connected to the liquid transfer unit 18 in a non-releasable and irreversible manner, for example via a one-way locking mechanism. In a variant, said locking mechanism may be arranged between the second constituent container 4 and the liquid transfer unit 16, connecting the second constituent container 4 to the liquid transfer unit 16 in a non-releasable manner.

In another variant the filled pouch containing the diluent may be an integrated part of the single-use liquid transfer unit.

The locking mechanism may comprise various configurations such as a helical thread configured such that the container screws onto the liquid transfer unit, or a bayonet type coupling, or elastic or compliant latch arms with locking shoulders engaging complementary locking shoulders on the container, or a tight friction fit between the container docking end and the side wall of the liquid transfer unit docking cavity. The locking mechanism of the first container may differ from the locking mechanism of the second container, or may be similar. Irreversibility of the locking connection may be provided by latching shoulders or protrusions that allow relative displacement between components in one direction but block relative displacement in the reverse direction without destruction of the locking mechanism.

The first and second constituent containers 2, 4 each comprise a sealed transfer interface 10, 14. The sealed transfer interface 10, 14 may be a septum, a Luer connector or a cap with a valve mechanism. The sealed transfer interface 10, 14 may be protected by a cap or film of material to avoid damage and maintain sterility during transport and storage.

The container docking or coupling interface 30 comprises a first container docking interface 42 and a second container docking interface 44. The first and second container docking interfaces 42, 44 are configured to engage with the corresponding first and second sealed transfer interfaces 10, 14 of the first and second constituent containers 2, 4. In an advantageous variant, the first and second docking interfaces and respective connection ends of the containers have different shapes or profiles and/or sizes configured to prevent connection of the solvent-containing container in the docking interface of the active substance-containing container and vice versa. In FIGS. 1, 2, 3 and 6 the container docking interfaces 42, 44 each comprise a fluid coupling portion 54, 58 that in the illustrated embodiments comprises a piercing member 68, 70 configured to pierce a septum of the respective container. In a variant, a piercing member 68, 70 may be mounted on the first and second constituent containers 2, 4, configured to pierce a septum on the container docking interface 42, 44 of the liquid transfer unit 18.

In a further variant, the fluid coupling portion 54, 58 may comprise a female or male Luer connector which is connectable to a complementary male or female Luer connector mounted on the container 2, 4. The fluid coupling portion may however also comprise other configurations for sealed fluidic coupling between the container and the liquid transfer unit, such as a tube insertable in in a seal-tight manner through a corresponding orifice provided with a pressure threshold release valve or a valve opened by the coupling action.

Figure 6:
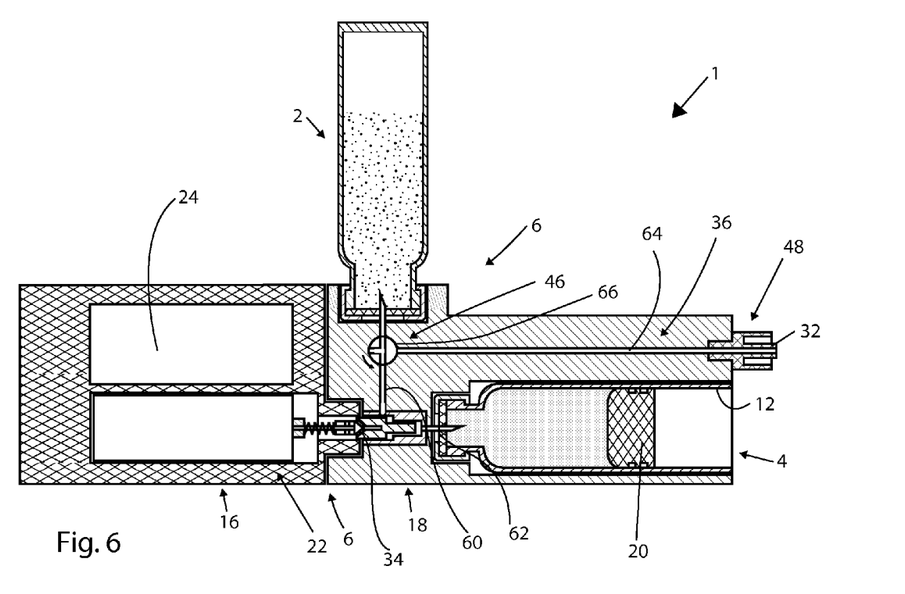
FIG. 6 is a cross-sectional view of another embodiment of a drug reconstitution device according to the invention.

The housing 26 comprises a fluid flow system 36 which in the embodiment illustrated in FIG. 6 comprises a first fluidic channel section 60, a second fluidic channel section 62 and a third fluidic channel section 64. The fluid flow system 36 may also comprise a valve mechanism 46 with a three-way valve 66 and the external connecting portion 48, as best seen in FIG. 6. The first fluidic channel section 60 interconnects the first container docking interface 42 of the first constituent container 2 fluidically with the pump chamber 41 and the second fluidic channel section 62 interconnects the second container docking interface 44 of the second constituent container 4 fluidically with the pump chamber 41, as seen for example in FIGS. 1-3 and 6. The third fluidic channel 64 interconnects the three-way valve 66 and an external connecting portion 48. The three-way valve 66 is configured to be activated by the user or automatically after the lyophilized substance is dissolved in the solvent or diluent, for example via a user interface 24 on the control and drive unit 16. The reconstituted drug can then be delivered to a patient via the external infusion set 32 or to the connecting portion 48 for filling up a cartridge of a syringe. In order to avoid possible false manipulation, it might be of advantage, for example in a hospital, to provide a drug reconstitution system 1 configured to deliver the reconstituted drug automatically to an infusion set 32 or an injection system.

Exemplary ways of connecting the pump engine 28 to the pump drive 22 are schematically illustrated in FIGS. 4 and 5. FIG. 4 shows a mechanical connection with a shaft of the pump drive comprising a transmission output coupling 34 in the shape of a cross, star, bar or other shape configured to transmit torque which engages in a corresponding cavity of the transmission input coupling 50 of the rotor 38. A spring ensures that the transmission output coupling 34 of the pump drive is resiliently biased against and engages with the transmission input coupling 50 of the rotor 38.

FIG. 5 schematically illustrates a magnetic coupling between the rotor 38 and the pump drive 22. The transmission input coupling 50 comprises permanent magnets configured to magnetically couple with the magnetic field generated by the transmission output coupling 34. The magnetic field of the transmission output coupling may either be generated by electromagnets, or by permanent magnets mounted on a rotatable drive shaft.

The releasable fixing mechanism provided to hold the control and drive unit 16 to the disposable liquid transfer unit 18 during the drug reconstitution process may comprise a mechanical attachment mechanism such as releasable latches or clips, or a rotatable thread or bayonet coupling, or other mechanical mechanisms (not shown), or may comprise a magnetic coupling.

The disposable liquid transfer unit 18 may be connected to the control and drive unit 16 before the first or second constituent containers 2, 4 are connected to said liquid transfer unit 18.

Within the scope of the invention, it is possible to have one of the containers, in particular the solvent or diluent-containing container, pre-assembled or integrally formed with the disposable liquid transfer unit. In the latter variant, the liquid transfer unit may comprise a single docking interface for releasable connection to the container in which the solvent or diluent is pumped and the reconstituted drug is prepared.

The invention claimed is:

1. A drug reconstitution device comprising a single use disposable liquid transfer unit (18) and a reusable control and drive unit (16) removably connectable to the liquid transfer unit, the disposable liquid transfer unit including a housing (26), a docking interface (30) configured for coupling at least one of a first and a second constituent containers (2, 4) to the housing (10), and a pump engine (28) and fluid flow system (37) configured for transferring liquid from the first constituent container (2) to the second constituent container (4), the control and drive unit comprising a pump drive (22) configured to drive the pump engine during a fluid pumping action, the pump drive comprising a transmission output coupling (34) removably engaged with a transmission input coupling (50) of the pump engine (28) when the liquid transfer unit and control and drive unit are connected, wherein the pump engine is configured as a rotary pump and comprises a rotor rotatably moveable in a stator and integrated with said transmission input coupling (50), the transmission input coupling removably engageable with a transmission output coupling of the pump drive.

2. The drug reconstitution device according to claim 1, wherein the docking interface (30) comprises a first container docking interface (42) configured to interconnect the first constituent container with the fluid flow system (36) in a fluidic manner and a second container docking interface (44) configured to interconnect the second constituent container with the fluid flow system (36) in a fluidic manner.

3. The drug reconstitution device according to claim 2, wherein the first docking interface has a different shape or profile or size than the second docking interface, configured to prevent connection of the first constituent container in the second container docking interface and connection of the second constituent container in the first container docking interface.

4. The drug reconstitution device according to claim 2, wherein the fluid flow system (36) comprises a first fluidic channel (60) and a second fluidic channel (62) and the pump engine comprises a pump chamber (41), said first fluidic channel interconnecting the first container docking interface (42) with the pump chamber in a fluidic manner and said second fluidic channel interconnecting the second container docking interface (44) with the pump chamber (41) in a fluidic manner.

5. The drug reconstitution device according to claim 1, wherein the docking interface comprises a locking mechanism configured to lock at least one of the first and second constituent containers to the housing when said constituent container is connected to the docking interface.

6. The drug reconstitution device according to claim 5, wherein the first container docking interface (42) comprises a locking mechanism (52) configured to lock the first constituent container (2) to the housing (26) when said constituent container is connected to the first container docking interface.

7. The drug reconstitution device according to claim 6, wherein at least one of said locking mechanism is irreversible and configured to irremovably couple at least one of said containers to the liquid transfer unit.

8. The drug reconstitution device according to claim 1, wherein the pump engine is configured as a bi-directional pump.

9. The drug reconstitution device according to claim 1, wherein the pump engine is configured as a uni-directional pump.

10. The drug reconstitution device according to claim 1 configured as a portable device, the control and drive unit comprising an autonomous power source.

11. The drug reconstitution device according to claim 1, wherein the device comprises a releasable locking mechanism configured to lock the control and drive unit to the liquid transfer unit during a liquid transfer operation.

12. The drug reconstitution device according to claim 1, wherein the pump engine rotor is directly attached to the transmission input coupling.

13. A drug reconstitution device comprising a single use disposable liquid transfer unit 18 and a reusable control and drive unit (16) removably connectable to the liquid transfer unit, the disposable liquid transfer unit including a housing (26), a docking interface (30) configured for coupling at least one of a first and a second constituent containers (2, 4) to the housing (10), and a pump engine (28) and fluid flow system (37) configured for transferring liquid from the first constituent container (2) to the second constituent container (4), the control and drive unit comprising au drive (22) configured to drive the pump engine during a fluid pumping action, the pump drive comprising a transmission output coupling (34) removably engaged with a transmission input coupling (50) of the pump engine (28) when the liquid transfer unit and control and drive unit are connected, wherein the pump engine is configured as a rotary pump and comprises a rotor rotatably moveable in a stator and integrated with said transmission input coupling (50), the transmission input coupling removably engageable with a transmission output coupling of the pump drive, wherein the transmission output coupling (34) is in the form of a spring biased shaft.

14. The drug reconstitution device according to claim 13, wherein the docking interface comprises a first container docking interface configured to interconnect the first constituent container with the fluid flow system in a fluidic manner and a second container docking interface configured to interconnect the second constituent container with the fluid flow system in a fluidic manner.

15. The drug reconstitution device according to claim 14, wherein the first docking interface has a different shape or profile or size than the second docking interface, configured to prevent connection of the first constituent container in the second container docking interface and connection of the second constituent container in the first container docking interface.

16. The drug reconstitution device according to claim 14, wherein the fluid flow system comprises a first fluidic channel and a second fluidic channel and the pump engine comprises a pump chamber, said first fluidic channel interconnecting the first container docking interface with the pump chamber in a fluidic manner and said second fluidic channel interconnecting the second container docking interface with the pump chamber in a fluidic manner.

17. The drug reconstitution device according to claim 13, wherein the docking interface comprises a locking mechanism configured to lock at least one of the first and second constituent containers to the housing when said constituent container is connected to the docking interface.

18. The drug reconstitution device according to claim 17, wherein the first container docking interface comprises a locking mechanism configured to lock the first constituent container to the housing when said constituent container is connected to the first container docking interface.

19. The drug reconstitution device according to claim 18, wherein at least one of said locking mechanism is irreversible and configured to irremovably couple at least one of said containers to the liquid transfer unit.

20. The drug reconstitution device according to claim 13, wherein the pump engine is configured as a bi-directional pump.

21. The drug reconstitution device according to claim 13, wherein the pump engine is configured as a uni-directional pump.

22. The drug reconstitution device according to claim 13 configured as a portable device, the control and drive unit comprising an autonomous power source.

23. The drug reconstitution device according to claim 13, wherein the device comprises a releasable locking mechanism configured to lock the control and drive unit to the liquid transfer unit during a liquid transfer operation.

24. The drug reconstitution device according to claim 13, wherein the pump engine rotor is directly attached to the transmission input coupling.

25. A drug reconstitution device comprising a single use disposable liquid transfer unit (18) and a reusable control and drive unit (16) removably connectable to the liquid transfer unit, the disposable liquid transfer unit including a housing (26), a docking interface (30) configured for coupling at least one of first and second constituent containers (2, 4) to the housing (10), and a pump engine (28) and fluid flow system (37) configured for transferring liquid from the first constituent container (2) to the second constituent container (4), the control and drive unit comprising a pump drive (22) configured to drive the pump engine during a fluid pumping action, the pump drive comprising a transmission output coupling (34) removably engaged with a transmission input coupling (50) of the pump engine (28) when the liquid transfer unit and control and drive unit are connected, wherein the pump engine is integrally mounted in the liquid transfer unit (18) and is configured as a bi-directional rotary pump and comprises a rotor rotatably moveable in a stator and integrated with said transmission input coupling (50), the transmission input coupling removably engageable with a transmission output coupling of the pump drive.

26. The drug reconstitution device according to claim 25, wherein the docking interface comprises a first container docking interface configured to interconnect the first constituent container with the fluid flow system in a fluidic manner and a second container docking interface configured to interconnect the second constituent container with the fluid flow system in a fluidic manner.

27. The drug reconstitution device according to claim 26, wherein the first docking interface has a different shape or profile or size than the second docking interface, configured to prevent connection of the first constituent container in the second container docking interface and connection of the second constituent container in the first container docking interface.

28. The drug reconstitution device according to claim 26, wherein the fluid flow system comprises a first fluidic channel and a second fluidic channel and the pump engine comprises a pump chamber, said first fluidic channel interconnecting the first container docking interface with the pump chamber in a fluidic manner and said second fluidic channel interconnecting the second container docking interface with the pump chamber in a fluidic manner.

29. The drug reconstitution device according to claim 25, wherein the docking interface comprises a locking mechanism configured to lock at least one of the first and second constituent containers to the housing when said constituent container is connected to the docking interface.

30. The drug reconstitution device according to claim 29, wherein the first container docking interface comprises a locking mechanism configured to lock the first constituent container to the housing when said constituent container is connected to the first container docking interface.

31. The drug reconstitution device according to claim 30, wherein at least one of said locking mechanism is irreversible and configured to irremovably couple at least one of said containers to the liquid transfer unit.

32. The drug reconstitution device according to claim 25 configured as a portable device, the control and drive unit comprising an autonomous power source.

33. The drug reconstitution device according to claim 25, wherein the device comprises a releasable locking mechanism configured to lock the control and drive unit to the liquid transfer unit during a liquid transfer operation.

34. The drug reconstitution device according to claim 25, wherein the pump engine rotor is directly attached to the transmission input coupling.

* * * * *